United States Patent [19]

Nefedov et al.

[11] Patent Number: 4,458,202

[45] Date of Patent: Jul. 3, 1984

[54] DEVICE FOR MEASURING LOCAL ELECTRIC CONDUCTIVITY OF LOW-TEMPERATURE PLASMA

[75] Inventors: Anatoly P. Nefedov; Felix M. Oherman; Jury G. Katoshin; Semen I. Krugly; Gennady P. Maljuzhonok and Jurz S. Mikhailov; all of Moscow, U.S.S.R.

[73] Assignee: Institut Vysokikh Temperatur Akademii Nauk SSSR, Moscow, U.S.S.R.

[21] Appl. No.: 303,187

[22] Filed: Sep. 17, 1981

[51] Int. Cl.³ ..................... G01N 27/74; G01R 33/12
[52] U.S. Cl. .................................. 324/204; 324/202; 324/236; 324/262; 324/445
[58] Field of Search ............... 324/202, 204, 234, 236, 324/262, 445, 446, 71.1, 71.3, 72, 72.5

[56] References Cited

U.S. PATENT DOCUMENTS 3,152,303 10/1964 Lary et al. ..................... 324/236

Primary Examiner—Gerard R. Strecker
Assistant Examiner—Walter E. Snow
Attorney, Agent, or Firm—Holman & Stern

[57] ABSTRACT

A device for measuring local electric conductivity of plasma, comprising a probe, which is kinematically coupled to a drive mechanism and has a series circuit including an inductive sensor, a measuring oscillator, and a detector having one output coupled, via an optoelectronic converter, to a differential stage having a switch and a memory member. An output of the differential stage is coupled to one input of a measurement recording unit having another input coupled to a unit for feeding commands which is electrically coupled to an electropneumatic control unit accommodating air valves of drive mechanisms of the probe and calibration crystal, the air valve being coupled to pneumatic cylinders of the drive mechanisms by means of flexible bases made of an insulating material.

10 Claims, 6 Drawing Figures

DEVICE FOR MEASURING LOCAL ELECTRIC CONDUCTIVITY OF LOW-TEMPERATURE PLASMA

The invention relates to the measuring technology, and more particularly, to devices for measuring local electric conductivity of plasma.

FIELD OF APPLICATION

The invention may be used for measuring electric conductivity of low-temperature plasma in combustion chambers and in chambers of magnetohydrodynamic (MHD) generators, missile engines and other installations.

BACKGROUND OF THE INVENTION

Known in the art is a device for measuring average electric conductivity of plasma (cf. USSR Inventor's Certificate No. 577477, Cl. G 01 R 27/22, publ. in 1977), comprising an inductive sensor connected in a measuring circuit of a high-frequency oscillator and having a measuring coil and a compensation coil which are wound in a bifilar fashion, a detector, a recorder and a logical switching circuit connected to said coils through controlled switches.

In this device the inductive sensor of the straight way type is connected in the circuit of a high-frequency oscillator having a working frequency of about 200 kHz. The sensitive element of the sensor has two electrically identical bifilar coils of which one coil is a measuring coil and the other coil is a compensation coil. These coils are connected, via switches controlled by a logical switching circuit, to said high-frequency oscillator. The windings of the measuring coil are connected through one of the switches in opposition to one another and the windings of the compensation coil are concordantly connected through the other switch as one alternative. The sequence of switching of the bifilar windings in the prior art circuit consists in a cyclic switching of said controlled switches.

The disadvantages of the prior art device reside in the absence of possibility of measurement of local electric conductivity of plasma in local zones of about 1 to 10 mm and relatively low accuracy of measurements of average electric conductivity of plasma owing to instability of the high-frequency oscillator due to a non-linear variation of reactive component of the resistance of the windings of measuring circuit at working frequencies of hundreds kHz and at a temperature above 100° C.

Known in the art is also a device for measuring local electric conductivity of plasma (cf. N. A. Balashov et al., Studies of Temperature Dependence of Electric Conductivity of Working Fluid of Large MND Generators (in Russian), Teplofizika vysokikh temperatur, vol. 15, No. 6, 1977, p. 188). The device comprises a movable probe in the form of a wing-shaped rod made of a non-conductive material having at the end thereof an inductive sensor. The sensor is coupled, via a measuring oscillator and a detector, to a unit for recording measurements via a differential stage. The measuring oscillator, detector, differential stage and unit for recording measurements are arranged outside the movable probe. The probe is caused to move by means of a pneumatic probe drive mechanism. The calibration of the inductive sensor is effected during movement of the probe through the calibration unit made as an electrically conductive ring mounted at the end face of the pneumatic probe drive mechanism.

The probe movement is controlled by means of air valves of an electropneumatic control unit which are installed directly on the probe drive mechanism.

When high-frequency oscillations are generated in the coil of the inductive sensor, eddy currents are induced in the electrically conductive medium which cause a reduction of the Q factor of resonant oscillator circuit proportionally with the electric conductivity of the medium thus resulting in a decrease in the amplitude of self-oscillations of the measuring oscillator. A signal proportional with the amplitude of the measuring oscillator is detected in the control unit and is fed, via the differential stage, to the unit for recording measurements.

The disadvantage of the prior art device resides in that it is not possible to measure electric conductivity of plasma in the presence of strong magnetic fields (hundreds Gausses) which are characteristic of MHD generators, owing to possible misfunctions of electropneumatic elements of the probe drive system and some other systems of the device, such as the unit for recording measurements.

Such device has inadequate sensitivity and high error value (more than 5%) in measuring electric conductivity of plasma which is due to a limitation of maximum frequency of the measuring oscillator because of the need to arrange the electropneumatic control unit and measuring oscillator outside the probe.

The prior art device cannot have a local zone in which the electric conductivity of plasma is measured smaller than 100 mm which is not sufficient for an exact determination of the pattern of the electric conductivity, in particular, in the electrode zone of the channel of an MHD generator.

In addition, a Hall effect EMF developed in operation of an MHD generator does not make it possible to measure local electric conductivity owing to the absence of a high-potential uncoupling of measuring oscillator and recording unit.

Service life of the probe in measuring electric conductivity of plasma in the range of 2–30 S/m at a temperature up to 3200 K., e.g. in the combustion chamber of an MHD generator is very short and is about 20 measurements.

SUMMARY OF THE INVENTION

It is an object of the invention to improve the accuracy of measurements and reliability of the device in measuring local electric conductivity of plasma.

Further object of the invention is to reduce the size of a local zone in which electric conductivity is measured to 10 mm.

Still another object of the invention is to provide for operation of a device for measuring local electric conductivity of plasma in magnetic fields with magnetic flux up to 5 T.

Finally it is an object of the invention to prolong the service life of the probe and the device as a whole under the above-mentioned conditions for measuring electric conductivity during tens and hundreds hours of operation of an MHD generator with Hall-effect EMF of the order of 5 to 10 kV.

The invention resides in that in a device for measuring local electric conductivity of plasma, comprising a probe having at the end thereof an inductive sensor, a pneumatic probe drive mechanism, which is kinematically coupled to the probe, a measuring oscillator, a detector, a means for calibrating the inductive sensor, an electropneumatic control unit, and a measurement recording unit, which is coupled to the measuring sensor via a differential stage, according to the invention, there is provided a unit for feeding commands for calibration of the inductive sensor which is coupled to the means for calibrating the inductive sensor via the electropneumatic control unit, an optoelectronic converter having a power supply unit, a switch and a memory member, the series circuit including the inductive sensor, measuring oscillator in which the resonant oscillator circuit is formed by the inductive sensor, and the detector being accommodated in the probe casing, at the working end thereof, the output of the measuring oscillator being coupled, via the detector and optoelectronic converter, to one input of the differential stage having another input coupled to the memory member, both inputs of the differential stage being coupled to the switching circuit, and the inputs of the measurement recording unit being coupled to outputs of the unit for sending commands for calibration of the inductive sensor and of the differential stage.

This arrangement of the device makes it possible to measure the electric conductivity of plasma at a temperature up to 3000° C. in magnetic fields with magnetic flux of several T with a resolution of 1 to 10 mm and with a measurement error maximum 5%.

It is preferred to make in the device according to the invention the means for calibrating the inductive sensor in the form of a calibration semiconductor crystal having a reference electric conductivity which is secured to the end of a rod coupled to an individual drive mechanism. This facility makes it possible to lower to a large extent the error of measurement owing to the calibration of the transfer function of the system.

The power supply unit of the optoelectronic converter in the device according to the invention preferably comprises a high-potential transformer having an input connected to the high-frequency oscillator and an output connected to the optoelectronic converter via a stabilized rectifier converter. This facility enables the uncoupling of the power supply of the measuring oscillator and optoelectronic converter in respect of the Hall effect potential.

The drive mechanism of the means for calibrating the inductive sensor in the device according to the invention may be made in the form of a pneumatic cylinder, the calibration crystal being secured to the piston rod of the cylinder. An automatic calibration of the device can thus be performed immediately before and after measurements.

In order to ensure operability of the device under the conditions of a real MHD generator, air valves of the pneumatic probe drive mechanism and of the pneumatic calibration crystal drive mechanism combined into a common electropneumatic control unit, are preferably arranged outside the pneumatic cylinders of the drive mechanisms and coupled to the pneumatic cylinders by means of flexible hoses made of an insulating material.

A shield of the inductive sensor of the device according to the invention preferably comprises a bifilar noninductive coil wound over the coil of the inductive sensor proper and earthed at one point.

BRIEF DESCRIPTION OF THE DRAWINGS

Other objects and advantages of the invention will become apparent from the following detailed description of a specific embodiment with reference to the accompanying drawings, in which.

DETAILED DESCRIPTION OF THE INVENTION

Figure 1:
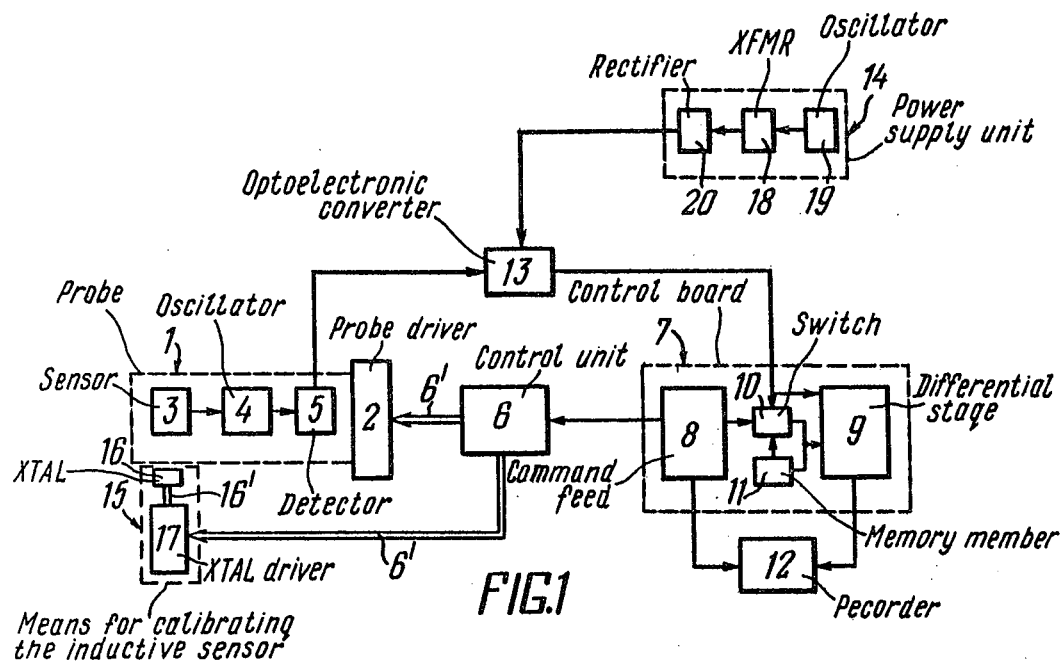
FIG. 1 is a block-diagram of a device for measuring local electric conductivity of plasma, according to the invention.

A device for measuring local electric conductivity of plasma comprises a wing-shaped probe 1 (FIG. 1) made in the form of an attachment to a piston rod (not shown in FIG. 1) of a pneumatic probe drive mechanism 2. Arranged in the interior of the probe, at the end thereof, are the following series connected devices: an inductive sensor 3, a measuring oscillator 4, and a detector 5 so that a parasitic capacitance from interconnections of the inductive sensor 3 with the measuring oscillator 4 is reduced thus improving the Q-factor of the inductive sensor 3 and the signal-to-noise ratio. The device also comprises an electropneumatic control unit 6 for controlling the pneumatic probe drive mechanism coupled to the drive mechanism 2 by means of flexible hoses 6' 10–15 m long which is arranged outside the zone of action of magnetic fields.

The electropneumatic control unit 6 is electrically coupled with its input to a control board 7 in which are accommodated a unit 8 for feeding commands which is designed for feeding a command for calibration of the inductive sensor 3 and a command for performing measurements, and a differential stage 9 coupled to a switch 10 and to a memory member 11. Two outputs of the unit 8 for feeding commands are connected to the input of the electropneumatic unit 6 and to one input of the switch 10 having another input which is connected to the memory member 11. The remaining output of the unit 8 and the output of the differential stage are connected to inputs of a unit 12 for recording measurements. The unit 12 for recording measurements comprises a standard loop oscillograph.

The connection of the differential stage 9 to the memory member 11 and switch 10 makes it possible to eliminate the influence of temperature, fluctuation and other factors causing instability on measurement results.

The measuring oscillator 4 is coupled, via the detector 5, to one input of an optoelectronic converter 13 having another input which is connected to a power supply unit 14. The optoelectronic converter 13 and the power supply unit 14 are arranged outside the casing of the probe 1 and drive mechanism 2. The output of the optoelectronic converter 13 is connected to the inputs of the switch 10 and differential circuit 9 which has another input coupled, via the memory member 11 and switch 10, to the output of the optoelectronic converter 13 for the time of measurement 100–300 ms. A means 15 for calibrating the inductive sensor comprises a calibrated semiconductor crystal 16 having a reference electric conductivity within the range from 5 to 20 S/m. The calibration crystal 16 is secured to the end of its rod 16' which is coupled to a drive mechanism 17 so as to ensure bringing the calibration crystal 16 during calibration close to the casing of the inductive sensor 350–500 ms immediately before and after the measurement.

The unit 14 for power supply of the optoelectronic converter 13 comprises a high-potential transformer 18 having input and output thereof which are connected to the output of a high-frequency oscillator 19 and to an input of a stabilized rectifier converter 20, respectively, the output of the rectifier converter being connected to the supply voltage input of the optoelectronic converter 13. This arrangement of the power supply unit 14 enables uncoupling of the circuit of the probe 1 and the optoelectronic converter 13 in respect of power supply.

The electropneumatic control unit 6, remote from the remaining units and devices, is connected to the drive mechanism 17 by means of flexible hoses 6' made of an insulating material.

Electric conductivity of the calibration crystal 16 should be chosen within the range from 5 to 20 S/m, because with the electric conductivity of the calibration crystal below 5 S/m or above 20 S/m the measurement results are hard to decode since the range of values of electric conductivity of plasma in channels of commercial MHD generators is from 1 to 20 S/m. The drive mechanism 17 has an adjustable "range", that is the adjustable distance from the calibration crystal 16 to the inductive sensor 3 so that any value of equivalent conductivity within the range from 5 to 20 S/m may be set at the moment of calibration. The drive mechanism 17 may be made in the form of a controlled pneumatic drive with the displacement time during calibration before and after measurements within the range of 50 to 500 ms during which calibration and synchronization of displacements of rods of the probe 1 and calibration crystal are performed.

Figure 2:
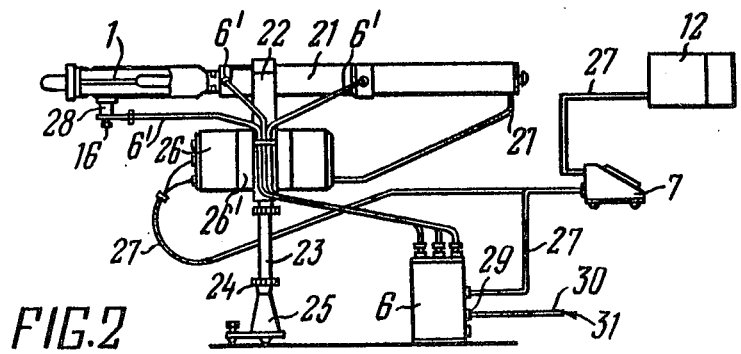
FIG. 2 schematically shows a structural arrangement of a device for measuring local electric conductivity of plasma, according to the invention.

FIG. 2 schematically shows a structural arrangement of a device for measuring local electric conductivity of plasma. The probe 1 has a wing-shaped configuration. The probe drive mechanism 2 comprises a pneumatic cylinder 21 which is installed on an insulating support 22. The insulating support 22 is installed on a telescopic rod 23 which is vertically adjustable by means of two nuts 24 and which is mounted on a base 25. The optoelectronic converter 13 (FIG. 1), together with the power supply unit 14, is accommodated in a cylindrical casing 26 (FIG. 2) having its middle part 26' made of an insulating material (glass) so as to provide a high-potential uncoupling of the measuring and recording parts of the device.

The optoelectronic converter 13 (FIG. 1) accommodated in the casing 26 (FIG. 2) is connected to the detector 5 (FIG. 1) of the probe 1 (FIG. 2) by means of an electric cable 27 extending inside the pneumatic cylinder 21 of the drive mechanism 2. The electric cable 27 also connects the optoelectronic converter 13 (FIG. 1) to the control board 7 (FIG. 2) and recording unit 12 and connects the control board 7 to the electropneumatic control unit 6.

Electric air valves of the drive mechanisms 17 and 2 of the calibration crystal and probe, respectively, are installed within the electropneumatic control unit 6, which is remote from the remaining part of the device, and are connected to pneumatic cylinders 28 and 21 of the drive mechanisms 17 and 2, respectively, by means of flexible hoses 6' which are 10 to 20 m long. The electropneumatic control unit 6 is started by the unit 8 (FIG. 1) for feeding commands from the control board 7, through the electric cable 27. Compressed air is supplied to the electropneumatic control unit 6 through an inlet pipe 29 and a flexible hose 30 (see arrow 31).

Figure 3:
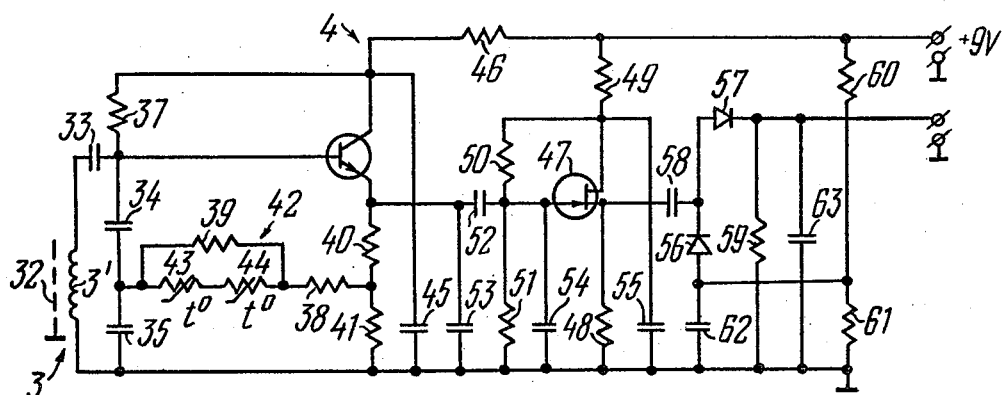
FIG. 3 is a wiring diagram of a measuring oscillator, inductive sensor, and detector, according to the invention.

FIG. 3 shows circuit diagrams of the inductive sensor 3, measuring oscillator 4, and detector 5.

The sensitive element of the inductive sensor 3 is a coil 3'; in addition, a shield 32 of the inductive coil 3 comprises a bifilar non-inductive coil which is wound over the coil 3' and earthed at one point so that measurements may be conducted in a plasma with high permittivity. The coil 3', in combination with capacitors 33,34,35 forms a resonant oscillator circuit around a transistor 36 operating as a current amplifier. Bias voltage is set by a resistor 37. This stage has an adequate stability owing to a strong negative feedback provided by resistors 38,39,40,41. However, in case the measuring oscillator 4 and sensor 3 are accommodated inside the probe 1 (FIG. 1), in the front end part thereof, which is subjected to thermal shocks, a substantial change of an active component of the coil 3' of the inductive sensor 3 (FIG. 3) may occur. A change in the value of active component of the coil 3' results in a change of the transfer function of the stage as a whole, hence in a change in sensitibity during measurement.

Various temperature changes are automatically compensated for by using a circuit 42 including temperature dependent resistors 43,44 with positive temperature dependence inserted in the feedback circuit of the measuring oscillator 4.

The power supply side of the oscillator 4 is uncoupled by means of a circuit including a capacitor 45 and a resistor 46.

To reduce the load imposed by the detector 5 on the measuring oscillator 4, a drain follower built around a field-effect transistor 47, resistors 48,49,50,51 and capacitors 52,53,54,55 is used. Signal is detected by diodes 56,57 with voltage doubling, in combination with a capacitor 58 and a resistor 59. The provision of a circuit including resistors 60,61 and capacitors 62,63 is mecessary to enable operation of the detector 5 at low voltages. Supply voltage from the unit 14 (FIG. 1) is fed to respective leads of the resistors 46,49,60 (FIG. 3), and the detected signal is taken from the resistors 59,61 forming RC circuits with capacitors 63 and 62.

Figure 4:
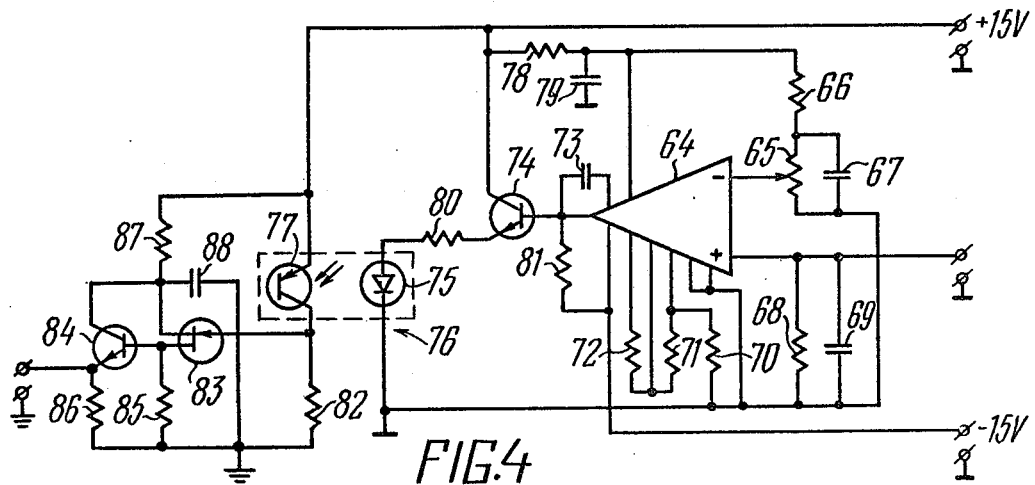
FIG. 4 is a wiring diagram of an optoelectronic converter according to the invention.

A circuit diagram of the optoelectronic converter 13 is shown in FIG. 4.

The detected voltage is fed from the output of the measuring oscillator 4 to the input of an operational amplifier 64. A pre-set d-c. reference voltage equal to minimum value of the detected voltage from the measuring oscillator 4 is fed to a second input of the operational amplifier 64 via a circuit including resistors 65,66 and a capacitor 67. The provision of a circuit including a resistor 68 and a capacitor 69 at the input of the operational amplifier 64 is necessary for selection of time constant of the detector 5 (FIG. 3). Balancing the operational amplifier 64 (FIG. 4) is made by means of a circuit including resistors 70,71,72. A correcting capacitor 73 is provided at the output of the operational amplifier 64. The use of the operational amplifier 64 is required by the need to improve the dynamic range and to amplify the data-bearing signal. The amplified difference voltage is fed, via an emitter amplifier built around a transistor 74, to a light-emitting diode 75 of a specially designed optronic couple 76 consisting of the light-emitting diode 75 and a phototransistor 77 for uncoupling the measuring oscillator 4 (FIG. 1) and the recording unit 12.

The transistor 74 (FIG. 4) with an RC-filter including a resistor 78 and a capacitor 79 provides a linear current through the light-emitting diode 75 depending on the input voltage of the transistor 74 and the value of resistance of a resistor 80. Bias voltage of the transistor 74 is set by a resistor 81. Output voltage of the phototransistor 77 is taken from a resistor 82. A combination drain-emitter follower built around transistors 83,84, resistors 85,86,87 and a capacitor 88 is used for matching the output of the phototransistor 77 to the remaining part of the circuit.

Figure 5:
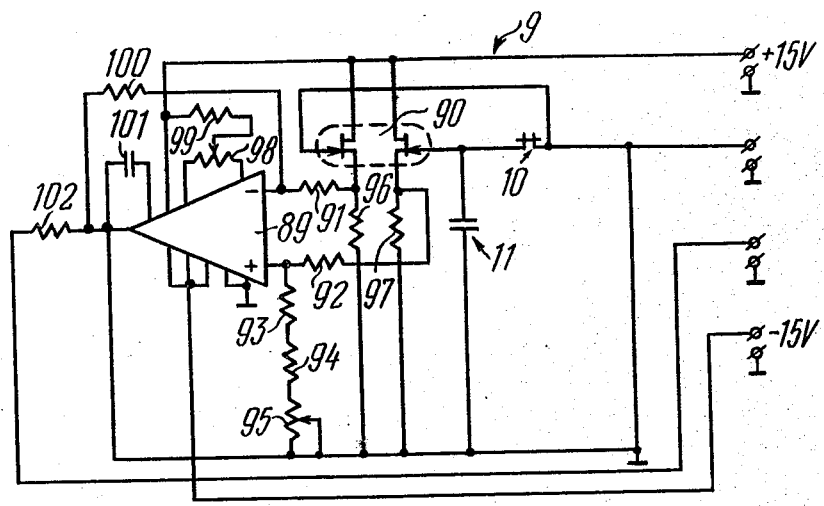
FIG. 5 is a wiring diagram of a differential stage, according to the invention.

A circuit diagram of the differential stage 9 is shown in FIG. 5.

To eliminate the influence of fluctuation and other slowly changing instability factors on measurement results, there is provided an operational amplifier 89 having its inputs connected to an output of a twin drain follower built around a twin field-effect transistor 90 with a very low gate current. A high-Q capacitor functioning as the memory member 11 is connected to one of the gates of the twin field-effect transistor 90, and the second gate of the transistor 90 is connected to the first gate via a normally closed switch 10. Signal from the measuring oscillator 4 (FIG. 1) is fed, via the optoelectronic converter 13, to the input of the switch 10. Operating function of the operational amplifier 89 (FIG. 5) and transistor 90 is set by selecting appropriate ratings of resistors 91,92,93,94,95,96,97,98,99,100. The ratio of ratings of the resistors 91 and 100 determines the transfer ratio of the stage. A correcting capacitor 101 is provided at the output of the operational amplifier 89. The output signal from the operational amplifier 89 is in the form of a voltage drop across a resistor 102.

Figure 6:
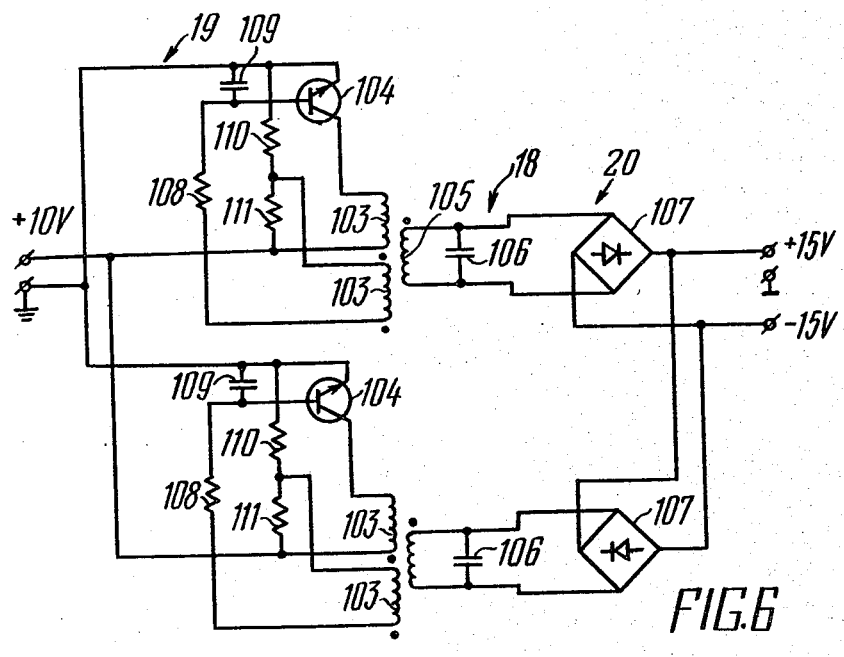
FIG. 6 is a wiring diagram of a power supply unit of an optoelectronic converter, according to the invention.

FIG. 6 shows a wiring diagram of the power supply unit 14 of the optoelectronic converter 13.

The power supply side is uncoupled by means of high-potential transformers 18. The transformers 18 are made without magnetic cores, and their primary windings 103 are inserted into the collector circuit of transistors 104 around which is built a high-frequency three-point oscillator 19. Voltage uncoupled with respect to potential is taken from circuits formed by secondary windings 105 of the transformers 18 and capacitors 106 and, after detection in bridge circuits 107, is fed for supplying the measuring oscillator 4 and the optoelectronic converter 13. Operating function of the measuring oscillator 4 is set by selecting ratings of resistor and capacitor 108 and 109. Feedback in the circuit is provided by a voltage divider consisting of resistors 110, 111 and the primary winding 103 of the high-potential transformer 18.

The device for measuring local electric conductivity of plasma functions cyclically in the following manner.

Upon feeding a signal for measurement from the unit 8 for feeding commands, the measurement recording unit 12 is turned on and, after a delay time of 100 ms, the drive mechanism 17 of the calibration crystal 16 is turned on. At the same time the signal of command for starting measurement is fed to the switch 10 so that the switch 10 opens, and a signal with an amplitude corresponding to the value stored in the memory member 11 which represents the ultimate value that occurred before the opening of the switch 10 is fed to the input of the differential stage 9 (the signal is fed from the optoelectronic converter 13). When the calibration crystal 16 having a reference conductivity approaches the inductive sensor 3, the Q-factor of the resonant circuit of the measuring oscillator 4 changes thus causing a change in the amplitude of oscillations of the measuring oscillator 4 and a change in the signal at the output of the detector 5 (that is at the input of the optoelectronic converter 13). The changing signal from the output of the optoelectronic converter 13 is fed to one input of the differential stage 9 and, from the output of the differential stage 9, to the recording unit 12. 200 ms after this, a signal from the unit 8 for feeding commands is fed, via the electropneumatic control unit 6, to the drive mechanism 17 so that the rod 16' of the calibration pneumatic cylinder 28 (FIG. 2) returns back to the initial position. After a delay time of 300 ms, following a signal from the electropneumatic control unit 6 (FIG. 1) fed to the probe drive mechanism 2, the inductive sensor 3 of the probe 1 enters a plasma in which electric conductivity is to be measured for a time of about 200 ms. When the inductive sensor 3 passes through a conducting medium, the Q-factor of the resonant circuit of the measuring oscillator 4 changes thus causing a change in signals at the outputs of the measuring oscillator 4, optoelectronic converter 13 and differential stage 9 in the same manner as during the calibration.

Changing signal from the output of the differential stage 9 is fed to the measurement recording unit 12 where it is held upon the appearance of a signal for recording from the command unit 8, during the entire measurement time. After the inductive sensor 3 has returned back into the initial position following a signal fed from the unit 8, a re-calibration of the device occurs which is completely similar to the calibration described above. All three phases of calibration and measurement results are recorded in the recording unit 12. The optoelectronic converter 13 is supplied through the stabilized rectifier converter 20 and high-potential transformer 18 from the high-frequency oscillator 19.

Operation of the differential stage 9 (FIG. 5) will be described in greater details.

During the period between measurements voltage at the output of the operational amplifier 89 is 0 independent of the level of the input signal. At the beginning of the measurement cycle the contact of relay of the switch 10 is opened, and the ultimate value of voltage from the output of the optoelectronic converter 13 (FIG. 1) is stored in the capacitor of the memory member 11. At the same time, a voltage which represents the result of measurement of a parameter being studied is fed to the second gate of the transistor 90 (FIG. 5). Therefore, the voltage at the output of the operational amplifier 89 changes from 0 to a value proportional with the parameter being measured during the measurement cycle. This voltage is recorded in the recording unit 12 (FIG. 1).

The distance from the electropneumatic control unit 6 (FIG. 2) to a magnet of an operating MHD plant, that is to the probe 1 should be about 10 to 20 m. The accuracy of measurement of the electric conductivity of plasma in the operating MHD generator is about 0.5%. The residence time of the sensor 3 in the plasma is less than 200 ms. The drive mechanism is supplied from a compressed air (nitrogen) bottle (not shown in FIG. 2) under a bottle pressure of minimum 50 atm. The probe 1 is cooled with compressed air under a pressure of 5 atm. The device is supplied from commercial frequency mains at 200 V±10%. Since the complete measurement time does not exceed 300 ms, a slow zero drift of matched elements (amplifiers and optoelectronic converter 13) has no effect on the accuracy of measurements. The unit 8 performs an automatic timing of operation of various parts of the device from the moment of starting until recording of output signals.

The device for measuring local electric conductivity of plasma according to the invention makes it possible to improve the accuracy of measurements and exhibits improved reliability. In addition, the device enables measurements to be conducted in the presence of strong magnetic fields at high induced Hall-effect EMF in real MHD generators at EMF values up to ten kV. The resolution of measurements in terms of the size of the local zone in which the parameter is measured is also improved by reducing the zone size to 10 mm.

We claim:

1. A device for measuring local electric conductivity of plasma, comprising:
   a probe;
   said probe having a casing and a working end;
   an inductive sensor provided at said working end of said probe;
   a drive mechanism of said probe which is kinematically coupled to the probe;
   a measuring oscillator accommodated in said casing of said probe;
   a detector having an input and an output, said detector being accommodated in said casing of said probe;
   said inductive sensor, measuring oscillator, and detector being electrically connected into a series circuit;
   an optoelectronic converter having two inputs and an output;
   a power supply unit of said optoelectronic converter coupled to one of said inputs of said optoelectronic converter;
   a differential stage having two inputs and an output;
   a switch having three inputs and an output;
   a memory member coupled to one of said inputs of said switch;
   the output of said optoelectronic converter being coupled to an input of said switch and an input of said differential stage;
   a second input of said optoelectronic converter being coupled to said output of said detector;
   the second input of said inputs of said differential stage being coupled to said inputs of said switch and memory member;
   a calibrating means for calibrating said inductive sensor;
   an electropneumatic control unit kinematically coupled to said drive mechanism of said probe and to said means for calibrating the inductive sensor;
   a unit for feeding commands for performing measurement and calibration;
   said unit for feeding commands having outputs;
   a unit for measurement recording having inputs;
   said outputs of said unit for feeding commands being coupled to the input of said electropneumatic control unit, to one of said inputs of said measurement recording unit, and to said third input of said switch, respectively;
   said output of said differential stage being coupled to the other of said inputs of said measurement recording unit.

2. A device as claimed in claim 1, comprising said power supply unit of said optoelectronic converter which is made in the form of a series circuit including a stabilized rectifier converter, a high-potential transformer, and a high-frequency oscillator;
   an output of said stabilized rectifier converter which is said output of the power supply unit being coupled to one of said inputs of said optoelectronic converter.

3. A device as claimed in claim 1, comprising said means for calibrating the inductive sensor which comprises a calibration semiconductor crystal;
   said calibration crystal having a reference electric conductivity;
   a rod for supporting said calibration crystal;
   said calibration crystal being secured to an end of said rod having a range adjustment capacity;
   a drive mechanism of said rod;
   said drive mechanism being kinematically coupled to said electropneumatic unit.

4. A device as claimed in claim 1, comprising:
   said inductive sensor having a shield and a coil;
   said shield comprising a bifilar non-inductive coil wound over said first coil of the inductive sensor.

5. A device as claimed in claim 2, comprising:
   said means for calibrating the inductive sensor having a calibration semiconductor crystal with a reference electric conductivity;
   said calibration crystal being secured to a rod;
   a drive mechanism of said calibrating means kinematically coupled to said rod;
   said drive mechanism of said calibrating means comprising a pneumatic cylinder.

6. A device as claimed in claim 2, comprising:
   a calibrating means drive mechanism;
   air valves of said probe and calibrating means drive mechanisms which are pneumatically coupled to the drive mechanisms;
   pneumatic cylinders of said drive mechanisms;
   said electropneumatic control unit including said air valves of said drive mechanisms;
   said air valves of said drive mechanisms being arranged outside said pneumatic cylinders of said drive mechanisms.

7. A device as claimed in claim 2, comprising:
   said inductive sensor having a shield and a coil;
   said shield comprising a bifilar non-inductive coil wound over said first coil of the inductive sensor.

8. A device as claimed in claim 3, comprising:
   said drive mechanism of the calibrating means comprising a pneumatic cylinder;
   said calibration crystal secured to a piston rod of said pneumatic cylinder.

9. A device as claimed in claim 3, comprising:
   said probe drive mechanism having air valves and a pneumatic cylinder;
   said drive mechanism of the calibrating means having air valves and comprising a pneumatic cylinder;
   said air valves of said drive mechanisms being arranged outside said pneumatic cylinders of said drive mechanisms and being accommodated in said electropneumatic control unit which is pneumatically coupled to said drive mechanisms.

10. A device as claimed in claim 3, comprising:
    said inductive sensor having a shield and a coil;
    said shield comprising a bifilar non-inductive coil wound over said first coil of the inductive sensor.

* * * * *